US00PP33282P3

(12) United States Plant Patent
Juneau

(10) Patent No.: US PP33,282 P3
(45) Date of Patent: Jul. 27, 2021

(54) GRAPE PLANT NAMED 'GEWURZTRAMINER RJ'

(50) Latin Name: *Vitis vinifera*
Varietal Denomination: Gewurztraminer RJ

(71) Applicant: Ronald Juneau, Pont-Rouge (CA)

(72) Inventor: Ronald Juneau, Pont-Rouge (CA)

( * ) Notice: Subject to any disclaimer, the term of this patent is extended or adjusted under 35 U.S.C. 154(b) by 0 days.

(21) Appl. No.: 16/873,713

(22) Filed: Jun. 10, 2020

(65) Prior Publication Data

US 2020/0396879 P1 Dec. 17, 2020

(30) Foreign Application Priority Data

Jun. 11, 2019 (CA) ..... PBR 19-9940

(51) Int. Cl.
*A01H 5/08* (2018.01)
*A01H 6/88* (2018.01)

(52) U.S. Cl.
USPC ..... Plt./206
CPC ..... *A01H 6/88* (2018.05)

(58) Field of Classification Search
USPC ..... Plt./156, 205, 206
See application file for complete search history.

(56) References Cited

U.S. PATENT DOCUMENTS

PP18,937 P2 * 6/2008 Sheehan ..... A01H 6/88
Plt./206

* cited by examiner

*Primary Examiner* — Susan McCormick Ewoldt
*Assistant Examiner* — Karen M Redden
(74) *Attorney, Agent, or Firm* — Penny J. Aguirre

(57) ABSTRACT

The invention is a new and distinct variety of Grapes plant named 'Gewurztraminer RJ' that is characterized by its grape clusters that are medium-large in size and cylindro-conical in shape, its good cold hardiness, its mature fruit early in the season, its vigorous growth habit with high fruit production, its grapes that are pink-purple in color at full maturity, good disease resistance, its grapes that have thick skins and are resistant to fall frost, and its grapes that produce wine that is rich in aroma and with a fruity taste.

2 Drawing Sheets

Botanical classification: *Vitis vinifera.*
Variety denomination: 'Gewurztraminer RJ'.

CROSS-REFERENCE TO A RELATED APPLICATION

This application claims priority to a Canadian plant breeders' rights application filed on Jun. 11, 2019, application No. 19-9940, under 35 U.S.C. 119(f), the entire contents of which is incorporated by reference herein.

BACKGROUND OF THE INVENTION

The present invention relates to a new and distinct cultivar of grape plant botanically known as *Vitis vinifera* 'Gewurztraminer RJ', referred to hereafter by its cultivar name, 'Gewurztraminer RJ'.

'Gewurztraminer RJ' arose as a natural branch mutation of *Vitis vinifera* 'Gewurztraminer' (not patented) in 1991 by the Inventor at his research site located in the county of Portneuf, Quebec, Canada.

Asexual propagation of the new cultivar was first accomplished by hardwood stem cuttings in 1999 by the Inventor in Port-Rouge, Québec, Canada. Asexual propagation of the new cultivar by hardwood stem cuttings and tissue culture has determined that the characteristics are stable and true to type in successive generations.

SUMMARY OF THE INVENTION

The following traits have been repeatedly observed and represent the characteristics of the new cultivar. These attributes in combination distinguish 'Gewurztraminer RJ' as a new and unique cultivar of *Vitis.*

1. 'Gewurztraminer RJ' exhibits grape clusters that are medium-large in size and cylindro-conical in shape.
2. 'Gewurztraminer RJ' exhibits good cold hardiness.
3. 'Gewurztraminer RJ' exhibits mature fruit early in the season.
4. 'Gewurztraminer RJ' exhibits a vigorous growth habit with high fruit production.
5. 'Gewurztraminer RJ' exhibits grapes that are pink-purple in color at full maturity.
6. 'Gewurztraminer RJ' exhibits good disease resistance.
7. 'Gewurztraminer RJ' exhibits grapes that have thick skins and are resistant to fall frost.
8. 'Gewurztraminer RJ' exhibits grapes that produce wine that is rich in aroma and with a fruity taste.

The parent plant of 'Gewurztraminer RJ', 'Gewurztraminer', differs from 'Gewurztraminer RJ' in having much less cold hardiness, in being more susceptible to disease, grape clusters that are smaller in size with less weight per cluster, a different leaf shape and grapes that are different in color. 'Gewurztraminer RJ' can also be compared to the *Vitis* hybrid cultivar 'Traminette' (not patented) and to the *Vitis vinifera* cultivar 'Gewurztraminer CL 643' (not patented). 'Traminette' is similar to 'Gewurztraminer RJ' in having grapes that produce wine with a similar structure and mouthfeel. 'Traminette' differs from 'Gewurztraminer RJ' in having leaves that are different in shape and appearance, grapes that are different in color in clusters that differ in shape, and in being much less cold hardy, in producing grapes later in the season, and in having less disease resistance. 'Gewurztraminer CL 643' is similar to 'Gewurztraminer RJ' in having grapes that produce wine that is fragrant, spicy, with good sugar levels, acid levels and PH balance. 'Gewurztraminer CL 643' differs from 'Gewurztraminer RJ' in having fruit that is different in color, berry size, and cluster size, leaves that are different in shape and leaf buds and young shoots that are different.

BRIEF DESCRIPTION OF THE DRAWINGS

The accompanying colored photographs illustrate the overall appearance and distinct characteristics of the new grape cultivar. The photographs were taken of plants of the new cultivar as grown outdoors in a field in Saint-Ubalde, Québec, Canada.

The photograph in FIG. 1 was taken of a plant 9 years in age as grafted onto *Vitis riparia* rootstock (not patented) and provides a side view of the plant habit of 'Gewurztraminer RJ'.

Figure 1:
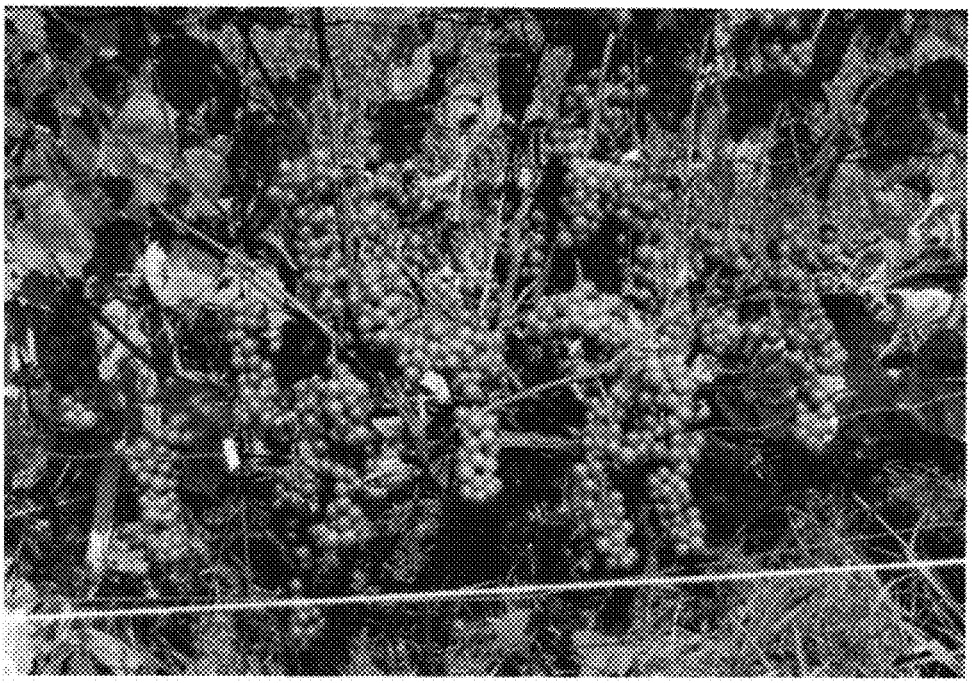
Figure 2:
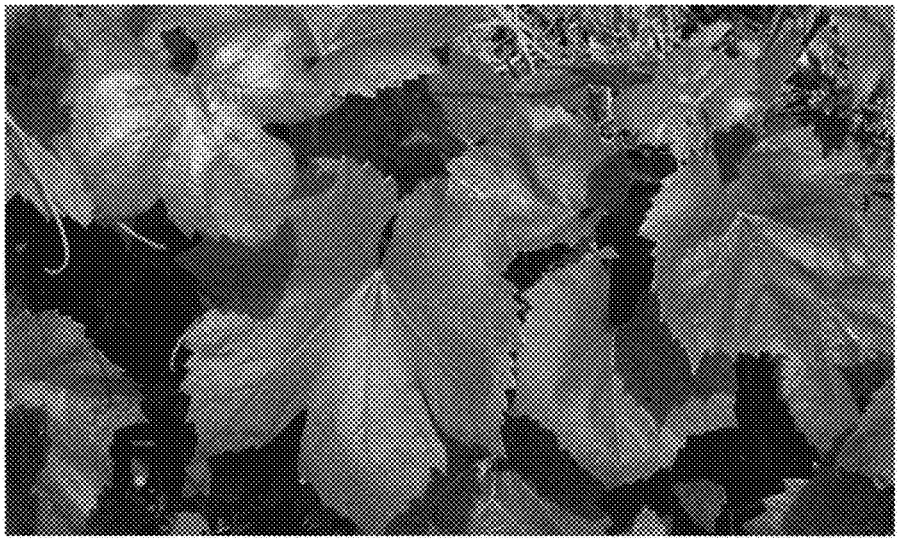

The photograph in FIG. 2 was taken of a plant 5 years in age as grafted onto *Vitis riparia* rootstock (not patented) and provides a close-up view of the foliage of 'Gewurztraminer RJ'.

Figure 3:
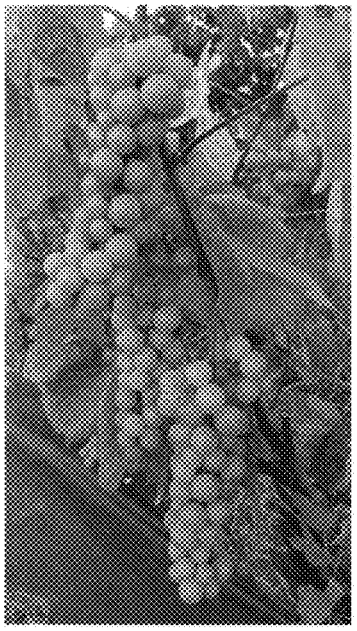
Figure 4:
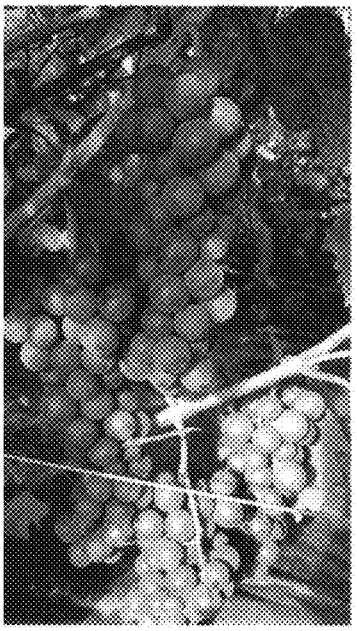

The photographs in FIG. 3 and FIG. 4 were taken of a plant 3 years in age (not grafted). The photograph in FIG. 3 provides a close-up view of the immature fruit of 'Gewurztraminer RJ'. The photograph in FIG. 4 provides a close-up view of the mature fruit of 'Gewurztraminer RJ'.

The colors in the photographs are as close as possible with digital photography techniques available, the color values cited in the detailed botanical description accurately describe the colors of the new cultivar of grape.

DETAILED BOTANICAL DESCRIPTION OF THE PLANT

The following is a detailed description of plants five years in age as grown outdoors in a trial field in Saint-Ubalde, Québec, Canada. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Typically commences blooms about June 24th in Pontneuf County, Québec, Canada.
*Plant type.*—Perennial fruit producing vine.
*Plant habit.*—Open but orderly.
*Height and spread.*—An average of 1.2 m in height and 220 cm in width.
*Cold hardiness.*—At least to U.S.D.A. Zone 4a.
*Propagation.*—Hardwood stem cuttings and tissue culture.
*Root description.*—Fibrous and fine.
*Root development.*—An average of 21 days for root initiation with a young plant produced from a rooted cutting in 45 to 60 days.
*Growth rate.*—Vigorous.

Cane description:

*Color of canes.*—A blend of 200B and 200C.
*Length of canes.*—1.5 m.
*Diameter of canes.*—1 cm.
*Internode length.*—12.5 cm.
*Lenticels.*—None observed.
*Cane cross-section shape.*—Round.
*Cane strength.*—Strong.
*Cane surface.*—Glabrous.
*Density of hairs on mature cane.*—None observed.
*Tendril pattern on shoot.*—2,0,2,0 etc. (two nodes with a tendril followed by one node without).
*Tendrils forked.*—Yes.
*Tendril texture.*—Glabrous.
*Tendril length.*—12 to 18 cm in length, 2-3 mm in width.
*Tendril color.*—On young shoots N144A to N144B, mature 144B to 144C.
*Bud width.*—3 mm.
*Bud length.*—5 mm.
*Bud shape.*—Triangular.
*Bud colour.*—144B.
*Bud burst.*—Medium to late.

Trunk description:

*Bark texture.*—Roughly striated.
*Bark colour.*—200C to 200D.

Leaf description:

*Length of blade.*—12.3 cm.
*Width of blade.*—12.9 cm.
*Shape of blade.*—Pentagonal to wedge-shaped.
*Leaf division.*—Simple.
*Leaf base.*—Cordate.
*Leaf apex.*—Acute.
*Leaf surface texture.*—Glabrous and smooth on upper and lower surface.
*Leaf attachment.*—Petiolate.
*Leaf arrangement.*—Alternate.
*Leaf number.*—An average of 5 per cane 16 cm in length.
*Number of lobes.*—3 to 5.
*Blade margins.*—Incised into lobes with lobes serrated.
*Length of primary (midrib) vein n1 from the tip of the blade to the petiole sinus.*—10.8 cm.
*Length of vein n2 from the tip of the first major lobe of the blade to the petiole sinus.*—9.8 cm.
*Length of vein n3 from the tip of the second major lobe of the blade to the petiole sinus.*—6.8 cm.
*Length of vein n4 from the tip of the third major lobe of the blade to where it joins the vein measured in n3.*—3.4 cm.
*Length of vein n5 from the tip of the first tooth proximal to the petiole sinus to where it joins the vein measured in n4.*—1.8 cm.
*Length of n2 teeth.*—0.75 cm.
*Width of n2 teeth.*—0.70 cm.
*Length/width ratio of n2 teeth.*—Small, 1:1.
*Length of n4 teeth.*—0.3 cm.
*Width of n4 teeth.*—0.2 cm.
*Length/width ratio of n4 teeth.*—Small, 1:1.
*Shape of teeth.*—Slightly convex.
*Shape of petiolar sinus.*—Half open.
*Shape of base of petiolar sinus.*—Narrow, v-shaped.
*Depth of petiolar sinus.*—3.5 cm.
*Width of petiolar sinus.*—1.2 cm.
*Petiole.*—12.29 cm in length, 2 to 3 mm in width, round, glabrous surface, color given on young shoot description.
*Shape of upper sinuses.*—Narrow v to u-shaped.
*Shape of base of upper sinuses.*—V-shaped.

*Pubescence on adaxial surface*.—None observed.
*Pubescence on abaxial surface*.—Very small erect hairs on veins.
*Color of adaxial leaf surface*.—A color between 144A and 146A.
*Color of abaxial leaf surface*.—146C to 146D.
*Color of leaf petiole*.—144A and 146A.
*Center lobe size*.—6.5 cm in length and 7.0 cm in width.
*Lateral lobe size*.—5.5 cm in length and width.

Young shoot description:
*Form of shoot tip*.—Slightly open.
*Density of prostate hairs on tip*.—Absent.
*Density of erect hairs on tip*.—Absent.
*Petiole pigmentation*.—A blend of N144C and N144D with 184C to 184D on sun exposed side.
*Shoot attitude* (*aspect*).—Erect.
*Shoot pigmentation* (*internodes and nodes*).—A blend of 144B and 144C and 184C and 184D on the ventral side exposed to the sun and 144B to 144C on the dorsal side.
*Young leaves*.—A blend of N144C and 144B to 144C in color with a slight suffusion of 184D on the upper surface, and N144C to N144D on the lower surface.

Flower description:
*Fragrance*.—Slightly fragrant.
*Mean time of flowering*.—About June 24 in Portneuf County, Québec, Canada.
*Color of calyx*.—143B.
*Sepal number*.—5, sepals fused into continuous calyx.
*Calyx shape*.—Ring-shaped.
*Calyx size*.—Length; <1 mm in, width; 2 mm.
*Calyx apex*.—Fused to ovary.
*Calyx base*.—Fused to pedicel.
*Calyx persistance*.—Not presistant.
*Nectary*.—1.5 mm in diameter, <1 mm in length, 143C in color.
*Calyx surface*.—Glabrous on both surfaces.
*Petals*.—5, fused in calyptra cohering at summit; 2.5 mm in width and 1 mm in depth and separating at base; 4 mm in width, 2 mm in depth; reflexed after dehiscence, 144A in color on both surfaces, glabrous on both surfaces, margins entire.
*Inflorescence type*.—Cluster.
*Inflorescence lastingness*.—About 2 weeks.
*Inflorescence size*.—About 10 cm in length and 2.5 cm in width at anthesis.
*Shape of cluster*.—Narrow to slightly conical, with shoulders.
*Number of flowers*.—Average of 150, 40 on wings if present.
*Flower buds*.—4 mm in length, 2.5 mm in width, a blend between 144B and N144C in color, oblanceolate in shape, glabrous surface.
*Size of individual entire flower*.—4 mm in height, 1.5 cm in width (to end of stamens).
*Pollen fertility*.—Fertile based on use in controlled crosses.
*Reproductive organs*.—Fully developed stamens and fully developed gynoecium.
*Color of stamen*.—Anther: 4D, filament: 160C to 160D.
*Stamen number*.—Average of 5.0.
*Filament length*.—5 mm.
*Anther*.—1.5 mm in length.
*Pollen quantity and color*.—Abundant and 10C in color.
*Pistil*.—1, ovary is 1.5 mm in length and 1 mm in width at base, inferior, urn-shaped, glabrous surface, color 144A to 144B, stigma is circular in shape, 1 mm in width and <1 mm in length, color 154C.
*Pedicel*.—3.5 mm and <1 mm in width, surface glabrous, colour 144C.
*Peduncle*.—To base of cluster 4.5 cm and 3 to 4 mm in width, glossy surface and 144A suffused with 184B.

Fruit description:
*Cluster length*.—19.8 cm.
*Cluster diameter*.—7.0 cm.
*Cluster weight*.—183 g.
*Cluster number*.—Average of 2.5 per cane.
*Cluster density*.—Dense, average of 139 berries per cluster.
*Berry weight*.—3.8 g.
*Berry length*.—1.8 cm.
*Berry diameter at equator*.—1.9 cm.
*Berry shape*.—Round.
*Berry cross-section*.—Circular (symmetrical).
*Berry skin thickness*.—Thick.
*Berry, color of skin*.—A blend of N186B and N186C.
*Berry, color of flesh*.—157A to 157B.
*Berry flesh texture*.—Smooth, juicy.
*Berry skin*.—Glabrous with slightly waxiness when mature.
*Berry firmness*.—Very firm.
*Berry, particular flavor*.—Sweet, not strongly aromatic.
*Length of pedicel*.—4 mm.
*Pedicel diameter*.—1.4 mm.
*Pedicel color*.—144B.
*Berry, separation from pedicel*.—Difficult.
*Berry, presence of seeds*.—Fully developed.
*Seed number/berry*.—2.
*Seed length*.—6.0 mm.
*Seed width*.—4.0 mm.
*Seed length/width ratio*.—Small, 1.5:1.
*Seed weight*.—0.03 g.
*Seed color*.—A blend of 199A and 199B.

Fruit chemistry: Values represent the means (with ranges in parentheses) for fruit harvested over five growing seasons 2016-2020.
*Harvest date*.—October 6 (October 1-12).
*Brix*.—18.3 (15-18.3).
*ph*.—3.31-3.40 (season 2020).
*Titratable acidity*.—8.2-11.92 (season 2020).
*Berry use*.—Wine production.
*Berry storage*.—Not applicable, used directly in wine making when ripe.
*Fruit set*.—High.

Vineyard performance: Based on observations compiled over five years (2016-2020).
*Susceptibility to powdery mildew* (*uncinula necator*).—None, presumed to be resistant.
*Susceptibility to downy mildew* (*plasmopara viticola*).—None, presumed to be resistant.
*Susceptibility to black rot* (*guignardia bidwellii*).—None, presumed to be resistant.
*Susceptibility to grey mold* (*botrytis cinerea*).—None.

*Susceptibility to foliar phylloxera* (*daktulosphaira vinfoliae*).—None present in Vineyard.
*Susceptibility to crown gall* (*agrobacterium tumefaciens*).—None.
*Susceptibility to phenoxy herbicide drift* (*e.g.*, 2,4-*d*).—None present in Vineyard.
*Pests*.—No susceptibility or resistance has been observed.
*Berry splitting*.—None.
*Berry shelling*.—None.
*Vigor level*.—High.
*Wood ripening*.—Good.

Wine characteristics:
*Flavors and aromas*.—Sugary taste with a slightly muscat flavor, with spicy notes.
*Balance*.—Well balanced.
*Color*.—White.
*Propensity for oxidation*.—None.
*Overall quality*.—Very good.

It is claimed:

1. A new and distinct cultivar of Grape plant named 'Gewurztraminer RJ' as herein illustrated and described.

* * * * *